US00PP22271P2

(12) United States Plant Patent
Psenner

(10) Patent No.: US PP22,271 P2
(45) Date of Patent: Nov. 22, 2011

(54) BIDENS PLANT NAMED 'BID 719'

(50) Latin Name: *Bidens triplinervia×Bidens ferulifolia*
Varietal Denomination: BID 719

(75) Inventor: Thomas Psenner, Bolzano (IT)

(73) Assignee: Amerinova Properties LLC, Bonsall, GA (US)

( * ) Notice: Subject to any disclaimer, the term of this patent is extended or adjusted under 35 U.S.C. 154(b) by 0 days.

(21) Appl. No.: 12/804,007

(22) Filed: Jul. 12, 2010

(51) Int. Cl.
*A01H 5/00* (2006.01)

(52) U.S. Cl. ..... Plt./410

(58) Field of Classification Search ..... Plt./410
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Bidens* plant named 'BID 719', characterized by its semi-upright, outwardly spreading to somewhat trailing plant habit; vigorous growth habit; freely flowering habit; large inflorescences with bright yellow-colored ray florets; and strong peduncles that hold the inflorescences above and beyond the foliar plane.

1 Drawing Sheet

Botanical designation: *Bidens triplinervia×Bidens ferulifolia.*

Cultivar denomination: 'BID 719'.

BACKGROUND OF THE INVENTION

The present invention relates to a new and distinct cultivar of *Bidens* plant, botanically known as *Bidens triplinervia× Bidens ferulifolia*, and hereinafter referred to by the name 'BID 719'.

The new *Bidens* is a product of a planned breeding program conducted by the Inventor in Bolzano, Italy. The objective of the breeding program was to develop new *Bidens* plants with attractive inflorescences with numerous ray florets.

The new *Bidens* plant originated from a cross-pollination made by the Inventor in Bolzano, Italy in 2007 of an unnamed selection of *Bidens triplinervia*, not patented, as the female, or seed, parent with *Bidens ferulifolia* 'Peters Goldteppich', disclosed in U.S. Plant Pat. No. 12,880, as the male, or pollen, parent. The new *Bidens* plant was discovered and selected by the Inventor as a single flowering plant from within the progeny of the stated cross-pollination grown in a controlled environment in Bolzano, Italy in August, 2007.

Asexual reproduction of the new *Bidens* by vegetative cuttings in a controlled environment in Bolzano, Italy since November, 2007, has shown that the unique features of this new *Bidens* plant are stable and reproduced true to type in successive generations.

SUMMARY OF THE INVENTION

Plants of the new *Bidens* have not been observed under all possible environmental conditions. The phenotype may vary somewhat with variations in environment such as temperature and light intensity, without, however, any variance in genotype.

The following traits have been repeatedly observed and are determined to be the unique characteristics of 'BID 719'. These characteristics in combination distinguish 'BID 719' as a new and distinct cultivar of *Bidens* plant:

1. Semi-upright, outwardly spreading to somewhat trailing plant habit.
2. Vigorous growth habit.
3. Freely flowering habit.
4. Large inflorescences with bright yellow-colored ray florets.
5. Strong peduncles that hold the inflorescences above and beyond the foliar plane.

Plants of the new *Bidens* differ from plants of the female parent, the unnamed selection of *Bidens triplinervia*, in the following characteristics:

1. Plants of the new *Bidens* have larger and darker green-colored leaves than plants of the female parent selection.
2. Plants of the new *Bidens* have larger inflorescences than plants of the female parent selection.
3. Inflorescences of plants of the new *Bidens* have more ray florets than inflorescences of plants of the female parent selection.

Plants of the new *Bidens* differ from plants of the male parent, 'Peters Goldteppich', in the following characteristics:

1. Young plants of the new *Bidens* are more upright than young plants of 'Peters Goldteppich'.
2. Inflorescences of plants of the new *Bidens* have more ray florets than inflorescences of plants of 'Peters Goldteppich'.

Plants of the new *Bidens* can be compared to plants of 'Bidcomtis', disclosed in U.S. Plant Pat. No. 17,326. In side-by-side comparisons conducted in Bolzano, Italy, plants of the new *Bidens* differed from plants of 'Bidcomtis' in the following characteristics:

1. Young plants of the new *Bidens* were more upright than young plants of 'Bidcomtis'.
2. Inflorescences of plants of the new *Bidens* had more ray florets than inflorescences of plants of 'Bidcomtis'.

BRIEF DESCRIPTION OF THE PHOTOGRAPHS

The accompanying photographs illustrate the overall appearance of the new *Bidens* plant. The photographs show the colors as true as it is reasonably possible to obtain in colored reproductions of this type. Colors in the photographs may differ slightly from the color values cited in the detailed botanical description which accurately describe the colors of the new *Bidens* plant.

The photograph at the bottom of the sheet comprises a side perspective view of a typical flowering plant of 'BID 719' grown in a container.

The photograph at the top of the sheet is a close-up view of a typical flowering plant of 'BID 719'.

DETAILED BOTANICAL DESCRIPTION

The aforementioned photographs and following observations and measurements describe plants grown during the summer in a polyethylene-covered greenhouse in Bonsall, Calif. and under conditions and practices which approximate those generally used in commercial *Bidens* production. During the production of the plants, day temperatures ranged from about 26° C. to 29° C., night temperatures ranged from 18° C. to 21° C. and light levels ranged from 8,000 to 10,000 foot-candles. Plants were pinched one time and were about 25 weeks old when the photographs and description were taken. In the following description, color references are made to The Royal Horticultural Society Colour Chart, 2007 Edition, except where general terms of ordinary dictionary significance are used.

Botanical classification: *Bidens triplinervia*×*Bidens ferulifolia* 'BID 719'.

Parentage:

*Female parent.*—Unnamed selection of *Bidens triplinervia*, not patented.

*Male parent.*—*Bidens ferulifolia* 'Peters Goldteppich', disclosed in U.S. Plant Pat. No. 12,880.

Propagation:

*Type.*—By vegetative cuttings.

*Time to initiate roots, summer.*—About 10 days at 16° C.

*Time to initiate roots, winter.*—About 14 days at 16° C.

*Time to produce a rooted young plant, summer.*—About 18 days at 16° C.

*Time to produce a rooted young plant, winter.*—About 21 days at 16° C.

*Root description.*—Fine, fleshy; white in color.

*Rooting habit.*—Moderate branching; moderately dense.

Plant description:

*Plant form/growth habit.*—Semi-upright, outwardly spreading to somewhat trailing plant habit; vigorous growth habit; freely branching habit with about six to eight primary lateral branches, each primary lateral branch with numerous lateral branches.

*Plant height.*—About 28 cm.

*Plant diameter or spread.*—About 61 cm.

*Lateral branches.*—Length: About 37 cm. Diameter: About 4 mm. Internode length: About 4 cm to 5 cm. Aspect: Upright, outwardly spreading or bending outwardly. Strength: Strong; flexible. Texture: Pubescent. Color: Close to 146C.

Foliage description:

*Arrangement.*—Opposite, simple.

*Length.*—About 3.2 cm.

*Width.*—About 3.8 cm.

*Shape.*—Roughly deltoid; pinnatisect.

*Apex.*—Acute.

*Base.*—Truncate.

*Margin.*—Deeply incised.

*Texture, upper and lower surfaces.*—Smooth, glabrous.

*Venation pattern.*—Pinnate.

*Color.*—Developing leaves, upper surface: Close to 137B. Developing leaves, lower surface: Close to 138A. Fully expanded leaves, upper surface: Close to N137C; venation, close to N137C. Fully expanded leaves, lower surface: Close to 147B; venation, close to 146C.

*Petiole length.*—About 1.5 cm.

*Petiole diameter.*—About 2 mm.

*Petiole texture, upper surface.*—Sparse pubescence.

*Petiole texture, lower surface.*—Smooth, glabrous.

*Petiole color, upper and lower surfaces.*—Close to 146C.

Inflorescence description:

*Appearance and flowering habit.*—Solitary rotate composite inflorescences that are either terminal or axillary; inflorescences are positioned above and beyond the foliar plane on strong peduncles; inflorescences face upright to outwardly; freely flowering habit with about 250 inflorescences developing per plant.

*Fragrance.*—None detected.

*Time to flower.*—Under natural season conditions, plants flower continuously from spring until the fall in Southern California; plants begin flowering about ten weeks after planting.

*Inflorescence longevity.*—Individual inflorescences last about one week on the plant; inflorescences persistent.

*Inflorescence bud.*—Height: About 1.3 cm. Diameter: About 1.1 cm. Shape: Ovoid. Color: Close to 15B with longitudinal stripes, close to 145A.

*Inflorescence size.*—Diameter: Large, about 4 cm. Depth (height): About 2 cm. Disc diameter: About 8 mm. Receptacle diameter: About 1.1 cm. Receptacle height: About 4 mm. Receptacle color: Close to 147A.

*Ray florets.*—Quantity/arrangement: About nine two-parted ray florets arranged in a single whorl; due to the two-parted structure of the ray floret, the ray florets appear to be arranged in a double whorl; the longer and broader outer part of the ray floret cups upwardly and outwardly with a recurved apex; the shorter and narrower inner part of the ray floret is mostly upright and located adjacent to the disc. Length, outer part of ray floret: About 2.1 cm. Width, outer part of ray floret: About 1.8 cm. Length, inner part of ray floret: About 1.9 cm. Width, inner part of ray floret: About 4 mm. Shape, outer part of ray floret: Obovate. Shape, inner part of ray floret: Oblanceolate. Apex, outer and inner parts of ray floret: Emarginate. Base, outer and inner parts of ray floret: Fused. Margin, outer and inner parts of ray floret: Entire. Texture, outer and inner parts of ray floret, upper and lower surfaces: Smooth, glabrous; velvety. Color, outer and inner parts of ray florets: When opening, upper surface: Close to 15A. When opening, lower surface: Close to 15C; fine longitudinal stripes, close to 145B. Fully opened, upper surface: Close to 13B. Fully opened, lower surface: Close to 13C; fine longitudinal stripes, close to 145B.

*Disc florets.*—Quantity/arrangement: About 86 massed at the center of the receptacle. Shape: Tubular; apex dentate. Length: About 8 mm. Diameter: About 1 mm. Texture: Smooth, glabrous. Color, immature: Apex: Close to N170B. Mid-section: Close to 153C. Base:

Close to 145B. Color, mature: Apex: Close to 7A. Mid-section: Close to 151D. Base: Close to 145C to 145D.

*Phyllaries.*—Quantity/arrangement: About 18 arranged in two whorls. Length: About 7 mm. Width: About 1 mm. Shape: Lanceolate. Apex: Acute. Base: Truncate. Margin: Entire. Texture, upper surface: Smooth, glabrous. Texture, lower surface: Pubescent. Color, upper surface: Close to 147A. Color, lower surface: Close to 147B.

*Peduncles.*—Length, terminal peduncles: About 6.4 cm. Length, axillary peduncles: About 7.1 cm. Diameter: About 1 mm. Strength: Strong; flexible. Aspect, terminal peduncles: Upright. Aspect, axillary peduncles: About 45° from vertical and curving upwardly. Texture: Pubescent. Color: Close to 146A.

*Reproductive organs.*—Androecium: Quantity per disc floret: Five. Filament length: About 4 mm. Filament color: Close to 145B. Anther shape: Lanceolate. Anther length: About 2 mm. Anther color: Close to 200A. Pollen amount: Scarce. Pollen color: Close to 21A.

*Gynoecium.*—Quantity per disc floret: One. Pistil length: About 8 mm. Stigma shape: Bi-parted. Stigma color: Close to 15A. Style length: About 5 mm. Style color: Close to 153D. Ovary color: Close to 145D.

Fruits/seeds: Fruit and seed development have not been observed on plants of the new *Bidens*.

Disease/pest resistance: Plants of the new *Bidens* have not been shown to be resistant to pathogens and pests common to *Bidens*.

Garden performance: Plants of the new *Bidens* have exhibited good tolerance to rain and wind and have been observed to tolerate temperatures from about 2° C. to about 45° C.

It is claimed:

1. A new and distinct *Bidens* plant named 'BID 719' as illustrated and described.

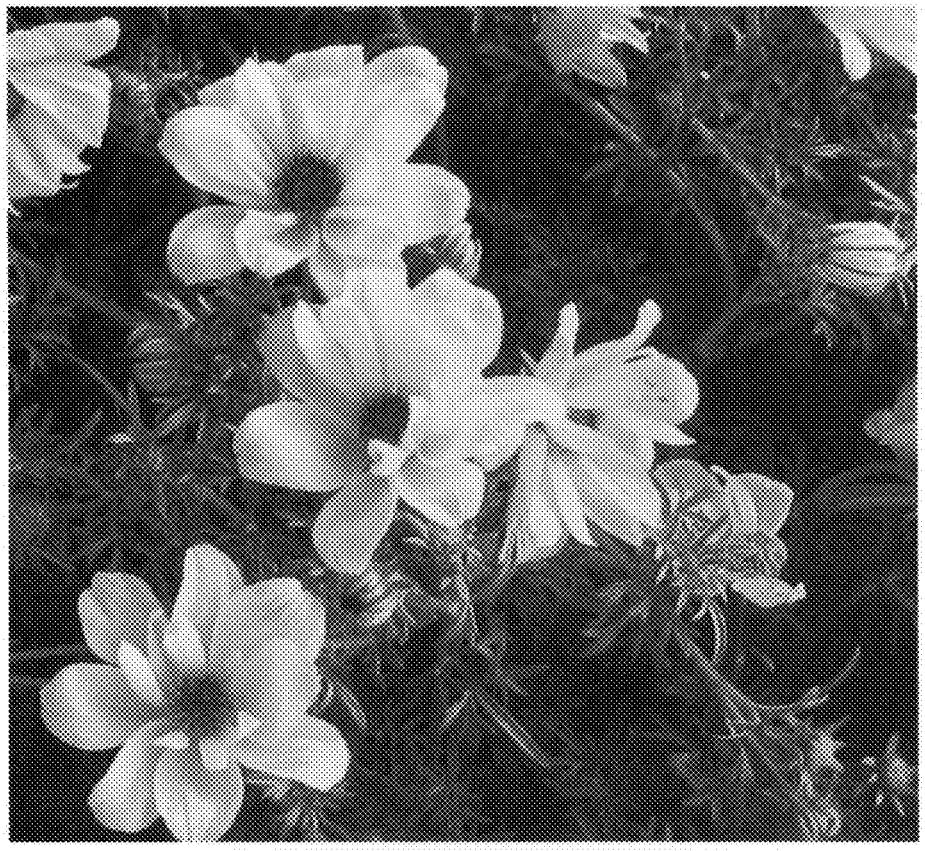
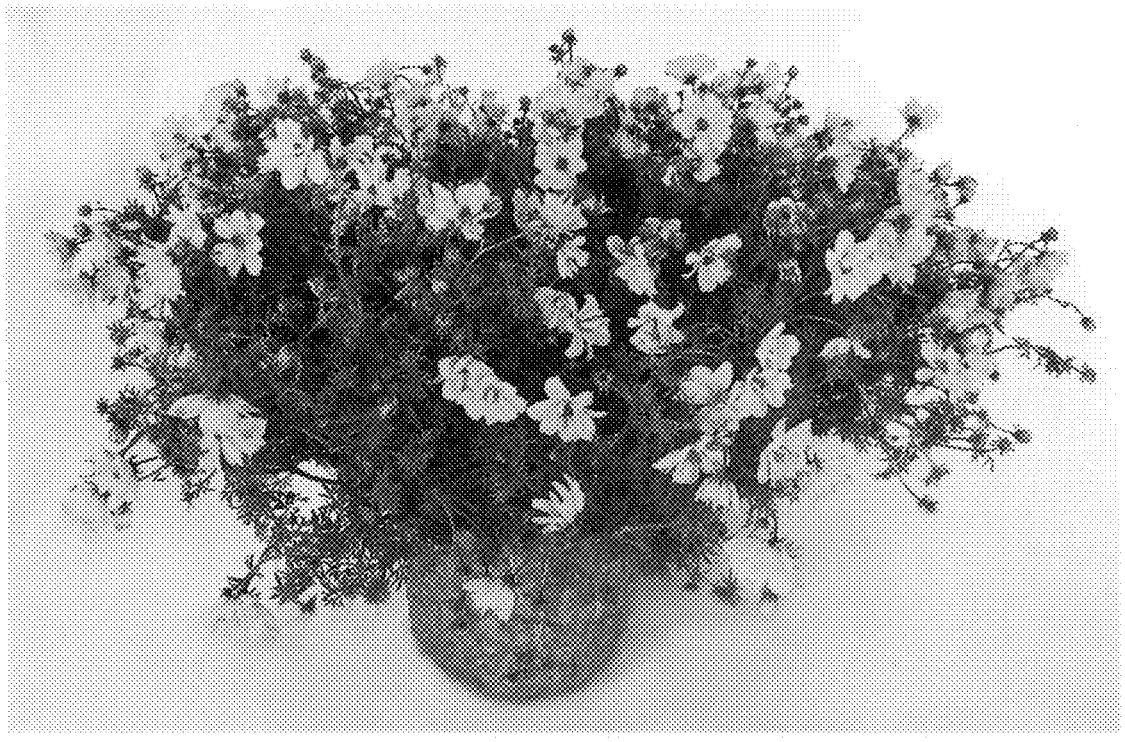

* * * * *